(12) United States Patent
Hahn et al.

(10) Patent No.: US 10,869,776 B2
(45) Date of Patent: Dec. 22, 2020

(54) KINESIOLOGY TAPE

(71) Applicant: KT HEALTH, LLC, Lindon, UT (US)

(72) Inventors: Gregory C. Hahn, Orem, UT (US); Ryan Dewey, Highland, UT (US); John Mackay, Alpine, UT (US)

(73) Assignee: KT Health, LLC, American Fork, UT (US)

(*) Notice: Subject to any disclaimer, the term of this patent is extended or adjusted under 35 U.S.C. 154(b) by 468 days.

(21) Appl. No.: 14/830,714

(22) Filed: Aug. 19, 2015

(65) Prior Publication Data
US 2016/0051393 A1    Feb. 25, 2016

Related U.S. Application Data

(60) Provisional application No. 62/039,330, filed on Aug. 19, 2014.

(51) Int. Cl.
| | | |
|---|---|---|
| A61F 5/40 | (2006.01) | |
| C09J 7/29 | (2018.01) | |
| C09J 7/21 | (2018.01) | |
| A61F 13/02 | (2006.01) | |

(52) U.S. Cl.
CPC .............. *A61F 5/40* (2013.01); *A61F 13/023* (2013.01); *C09J 7/21* (2018.01); *C09J 7/29* (2018.01); *C09J 2201/122* (2013.01); *C09J 2201/16* (2013.01); *C09J 2201/606* (2013.01); *C09J 2400/263* (2013.01)

(58) Field of Classification Search
CPC ...... A61F 13/00; A61F 15/005; A61F 13/023; A61F 5/40; C09J 7/29; C09J 2201/122; C09J 2201/16; C09J 2201/606; C09J 2400/263

USPC ...... 602/5, 6, 12, 16, 32, 41, 54, 60, 62, 75, 602/1; 606/199
See application file for complete search history.

(56) References Cited

U.S. PATENT DOCUMENTS

| | | |
|---|---|---|
| 1,441,708 A | 1/1923 | Overbury |
| 2,310,082 A | 2/1943 | Holbrooke |
| 2,349,709 A | 5/1944 | Evans |
| 2,399,545 A | 4/1946 | Davis |
| 2,508,855 A | 5/1950 | Brown |
| 2,646,040 A | 7/1953 | Stanton |
| 2,940,868 A | 6/1960 | Patchell |

(Continued)

FOREIGN PATENT DOCUMENTS

| | | |
|---|---|---|
| BE | 1002779 | 6/1991 |
| CN | 101616645 | 12/2009 |

(Continued)

OTHER PUBLICATIONS

Office Action dated Sep. 7, 2017 from U.S. Appl. No. 13/188,327.
(Continued)

*Primary Examiner* — Rachael E Bredefeld
*Assistant Examiner* — Caitlin A Carreiro
(74) *Attorney, Agent, or Firm* — Durham Jones & Pinegar, P.C., Intellectual Property Law Group

(57) ABSTRACT

Kinesiology tape may include a first layer of fabric with an adhesive on a first side of the first layer of fabric. The kinesiology tape may also include a second layer of fabric that may be coupled to the first layer of fabric. The first layer of fabric and the second layer of fabric may form a receiving portion and a support may be disposed in the receiving portion.

6 Claims, 10 Drawing Sheets

(56) References Cited

U.S. PATENT DOCUMENTS

| | | | |
|---|---|---|---|
| 2,957,475 A * | 10/1960 | Frances | A61F 13/04 |
| | | | 602/5 |
| 3,038,295 A | 6/1962 | Humpreys | |
| 3,199,548 A | 8/1965 | Conant | |
| 3,342,028 A | 9/1967 | Kanji et al. | |
| 3,355,974 A | 12/1967 | Carmichael | |
| 3,387,451 A | 6/1968 | Cape et al. | |
| 3,457,919 A | 7/1969 | Harbard | |
| 3,530,494 A | 9/1970 | Baratta | |
| 3,618,754 A | 11/1971 | Hoey | |
| 3,716,132 A | 2/1973 | Lewyckyj | |
| 3,965,786 A | 6/1976 | D'Luhy | |
| 3,989,041 A | 11/1976 | Davies | |
| 4,215,687 A | 8/1980 | Shaw | |
| 4,428,809 A | 1/1984 | Heimbach et al. | |
| 4,654,254 A | 3/1987 | Gerry et al. | |
| 4,734,320 A | 3/1988 | Ohira et al. | |
| 4,735,342 A | 4/1988 | Goldstein | |
| 4,737,400 A | 4/1988 | Edison | |
| 4,782,196 A | 11/1988 | Ukai | |
| 4,807,753 A | 2/1989 | Goldstein | |
| 5,230,701 A | 7/1993 | Meyer et al. | |
| 5,240,775 A | 8/1993 | Tannenbaum | |
| 5,397,298 A | 3/1995 | Mazza et al. | |
| 5,488,889 A | 2/1996 | Kang | |
| 5,496,605 A | 3/1996 | Augst et al. | |
| 5,537,905 A | 7/1996 | Zimmer et al. | |
| 5,755,681 A | 5/1998 | Plews | |
| 5,782,496 A | 7/1998 | Casper et al. | |
| 5,792,091 A | 8/1998 | Staudinger | |
| 5,861,348 A | 1/1999 | Kase | |
| 5,938,631 A | 8/1999 | Colma | |
| 5,981,823 A | 11/1999 | Turngren | |
| 6,007,468 A | 12/1999 | Giacometti | |
| D430,295 S | 8/2000 | Ierulli | |
| D434,146 S | 11/2000 | Ierulli | |
| 6,213,343 B1 | 4/2001 | Damikolas | |
| 6,422,848 B1 | 7/2002 | Allen et al. | |
| 6,447,470 B2 | 9/2002 | Bodenshatz et al. | |
| D484,603 S | 12/2003 | Kocik | |
| 6,756,519 B2 | 6/2004 | Johnson et al. | |
| 6,769,428 B2 * | 8/2004 | Cronk | A61F 5/08 |
| | | | 128/200.24 |
| 6,849,057 B2 | 2/2005 | Satou et al. | |
| 6,953,602 B2 | 10/2005 | Carte et al. | |
| 6,953,620 B2 | 10/2005 | Schneider et al. | |
| D516,728 S | 3/2006 | Wall | |
| 7,012,170 B1 | 3/2006 | Tomaioulo | |
| 7,146,893 B2 | 12/2006 | Aichele | |
| 7,419,476 B2 | 9/2008 | Oohira et al. | |
| 7,594,461 B2 | 9/2009 | Aichele et al. | |
| D604,856 S | 11/2009 | Arbesman et al. | |
| D607,114 S | 12/2009 | Arbesman et al. | |
| D608,007 S | 1/2010 | Arbesman et al. | |
| D608,453 S | 1/2010 | Arbesman et al. | |
| D608,893 S | 1/2010 | Arbesman et al. | |
| D608,894 S | 1/2010 | Arbesman et al. | |
| D608,896 S | 1/2010 | Arbesman et al. | |
| D609,354 S | 2/2010 | Arbesman et al. | |
| D612,505 S | 3/2010 | Arbesman et al. | |
| D612,506 S | 3/2010 | Arbesman et al. | |
| D612,507 S | 3/2010 | Arbesman et al. | |
| D612,508 S | 3/2010 | Arbesman et al. | |
| D612,944 S | 3/2010 | Arbesman et al. | |
| D613,414 S | 4/2010 | Arbesman et al. | |
| D613,415 S | 4/2010 | Arbesman et al. | |
| D616,553 S | 5/2010 | Arbesman et al. | |
| D616,998 S | 6/2010 | Arbesman et al. | |
| D621,051 S | 8/2010 | Kase | |
| D621,053 S | 8/2010 | Kase | |
| D621,518 S | 8/2010 | Arbesman et al. | |
| D622,403 S | 8/2010 | Arbesman et al. | |
| 7,790,420 B2 | 9/2010 | Hart, et al. | |
| D625,422 S | 10/2010 | Arbesman et al. | |
| D625,825 S | 10/2010 | Arbesman et al. | |
| D633,213 S | 2/2011 | Cowles | |
| 8,216,415 B2 | 7/2012 | Quinn | |
| D691,276 S | 10/2013 | Bushby | |
| D696,400 S | 12/2013 | Brogden | |
| 8,617,199 B2 | 12/2013 | Eull et al. | |
| D718,869 S | 12/2014 | Cameron | |
| D750,789 S | 3/2016 | Mackay et al. | |
| 9,308,115 B2 | 4/2016 | Quinn | |
| 2001/0056252 A1 | 12/2001 | Bodenschatz | |
| 2002/0040202 A1 | 4/2002 | Levin | |
| 2003/0069530 A1 | 4/2003 | Satou et al. | |
| 2003/0183053 A1 | 10/2003 | Amend et al. | |
| 2006/0065098 A1 | 3/2006 | Cranna | |
| 2006/0206047 A1 * | 9/2006 | Lampe | A61F 13/04 |
| | | | 602/42 |
| 2006/0206049 A1 * | 9/2006 | Rodgers | A61F 9/00781 |
| | | | 604/8 |
| 2007/0010777 A1 | 1/2007 | Dunshee et al. | |
| 2007/0073205 A1 | 3/2007 | Hull et al. | |
| 2007/0212520 A1 | 9/2007 | Furumori et al. | |
| 2008/0043085 A1 | 2/2008 | Einhorn | |
| 2008/0154169 A1 | 6/2008 | Kase | |
| 2008/0299855 A1 | 12/2008 | Morihashi | |
| 2009/0182256 A1 | 7/2009 | Lin | |
| 2009/0192256 A1 | 7/2009 | Takeda | |
| 2010/0016771 A1 | 1/2010 | Arbesman et al. | |
| 2010/0210988 A1 | 8/2010 | Dallison et al. | |
| 2010/0227102 A1 | 9/2010 | Keener et al. | |
| 2010/0277102 A1 | 11/2010 | Lin et al. | |
| 2010/0298747 A1 | 11/2010 | Quinn | |
| 2011/0275969 A1 * | 11/2011 | Quinn | A61F 5/40 |
| | | | 602/1 |
| 2013/0334084 A1 | 12/2013 | Arbesman | |
| 2014/0102632 A1 * | 4/2014 | Quinn | A61F 5/40 |
| | | | 156/248 |

FOREIGN PATENT DOCUMENTS

| | | |
|---|---|---|
| CN | 101822590 A | 9/2010 |
| CN | 102068338 | 5/2011 |
| CN | 202682161 U | 1/2013 |
| CN | 103826582 A | 5/2014 |
| DE | 825 448 | 12/1952 |
| DE | 1221091 | 7/1996 |
| FR | 2 896 808 | 8/2007 |
| GB | 953855 | 4/1964 |
| JP | 2004 248842 | 9/2004 |
| JP | 2008-136656 | 6/2008 |
| KR | 10-0802172 | 2/2008 |
| WO | 2006067876 | 6/2006 |
| WO | 2009-050493 A1 | 4/2009 |
| WO | 2013/011385 A2 | 1/2013 |
| WO | 2013-011385 A2 | 1/2013 |

OTHER PUBLICATIONS

Office Action dated Jun. 28, 2017 from U.S. Appl. No. 13/188,333.
Office Action dated Jun. 29, 2017 from U.S. Appl. No. 14/135,416.
Office Action dated Jul. 20, 2017 from Chinese Patent Application No. 201410359730.0 (English Translation).
Office Action dated May 30, 2017 from Canadian Patent Application No. 2720601.
Office Action dated May 31, 2017 from Chinese Patent Application No. 201280044120.0 (Machine Translation).
Office Action from Korean Patent Application No. 10-2010-0115392 dated Nov. 15, 2016.
Advisory Action from U.S. Appl. No. 14/135,416 dated Dec. 15, 2016.
Office Action from U.S. Appl. No. 13/188,333 dated Dec. 15, 2016.
Examiner's Report from Canadian Patent Application No. 2,845,061 dated Dec. 19, 2016.
Office Action from U.S. Appl. No. 13/188,327 dated Oct. 20, 2016.
U.S. Appl. No. 61/200,400, filed Nov. 26, 2008, Quinn.
U.S. Appl. No. 13/188,333, filed Jul. 21, 2011, Quinn.
U.S. Appl. No. 13/188,319, filed Jul. 21, 2011, Quinn.
U.S. Appl. No. 13/188,327, filed Jul. 21, 2011, Quinn.

(56) References Cited

OTHER PUBLICATIONS

U.S. Appl. No. 14/135,416, filed Dec. 19, 2013, Quinn.
U.S. Appl. No. 62/039,330, filed Aug. 19, 2014, Mackay, et al.
Kinesio Taping Perfect Manual.
Office Action from Chinese Patent Application 201280044120.0 dated Nov. 3, 2014.
Office Action from U.S. Appl. No. 13/188,319 dated May 6, 2014.
Office Action from U.S. Appl. No. 13/188,333 dated Jun. 9, 2014.
Office Action from U.S. Appl. No. 13/188,333 dated Sep. 14, 2012.
Office Action from U.S. Appl. No. 13/188,333 dated Oct. 8, 2013.
Office Action from U.S. Appl. No. 13/188,327 dated Nov. 8, 2013.
Office Action from U.S. Appl. No. 13/188,319, dated Dec. 11, 2014.
Office Action from Canadian Patent Application No. 2,845,061, dated Feb. 16, 2015.
Office Action from Korean Patent Application No. 10-2014-7004559, dated Jan. 6, 2015 (with English translation).
Supplemental European Search Report from EPO Appl. No. EP 12 81 4131 dated Mar. 12, 2015.
Office Action from Chinese Patent Application No. 201280044120.0 dated Sep. 6, 2015.
Office Action from U.S. Appl. No. 13/188,319 dated Sep. 28, 2015.
Examination Report from Australian Patent Application No. 2012285492 dated Jul. 15, 2015.
Notice of Allowance from U.S. Appl. No. 29/499,882 dated Oct. 13, 2015.
Examiner's Report from European Patent Application No. 12814131 dated Sep. 8, 2016.
Office Action from Chinese Patent Application No. 201410359730.0 dated Aug. 22, 2016 (with English Translation).
Examiner's Report from Canadian Patent Application No. 2720601 dated Aug. 16, 2016.
International Preliminary Report on Patentability from PCT/US2015/045972, dated Feb. 21, 2017.
Office Action from Chinese Patent Application No. 20140359730.0, dated Feb. 20, 2017.
EP Office Action dated Jul. 17, 2019 as received in Application No. 15833884.8.
CA Office Action dated Feb. 15, 2018 as received in Application No. 2,961,567.
CA Office Action dated Nov. 23, 2018 as received in Application No. 2,961,567.
EP Office Action dated Jan. 22, 2019 as received in Application No. 15833884.8.
USPTO as International Searching Authority, "International Search Report and Written Opinion," International application No. PCT/US2015/045972, dated Nov. 6, 2015.
European Patent Office, "Second Examination Report," European application No. EP15833884.8, dated Nov. 6, 2019.
Canadian Intellectual Property Office, "Examination Report," Canadian application No. 2961567, dated Aug. 28, 2019.
Chinese National Intellectual Property Administration, "Office Action," Chinese application No. 201580056178.0, dated Aug. 27, 2019.
CN First Office Action dated Aug. 27, 2019 as received in Application No. 201580056178.0.
CA Office Action dated Aug. 28, 2019 as received in Application No. 2961567.
Chinese National Intellectual Property Administration, "Second Office Action," Chinese patent application No. 201580056178.0, dated May 8, 2020.
European Patent Office, "Examination Report," European patent application No. 15833884.8, dated Mar. 30, 2020.

\* cited by examiner

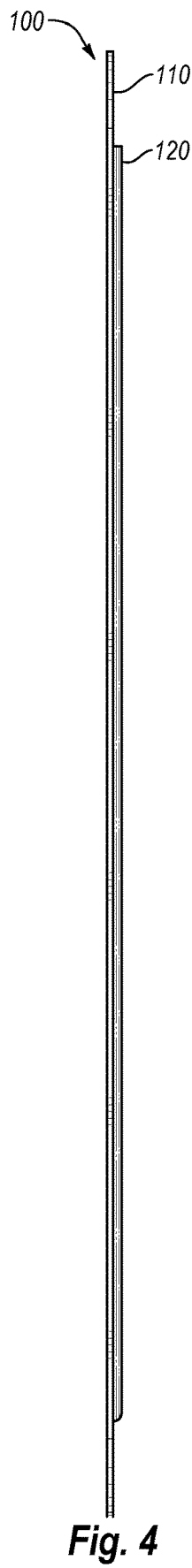
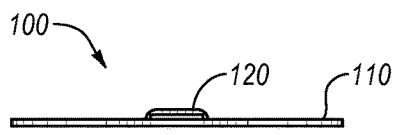
*Fig. 6*
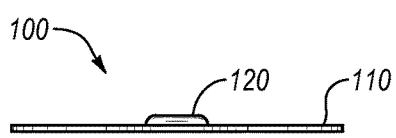
*Fig. 7*
*Fig. 4*  *Fig. 5*

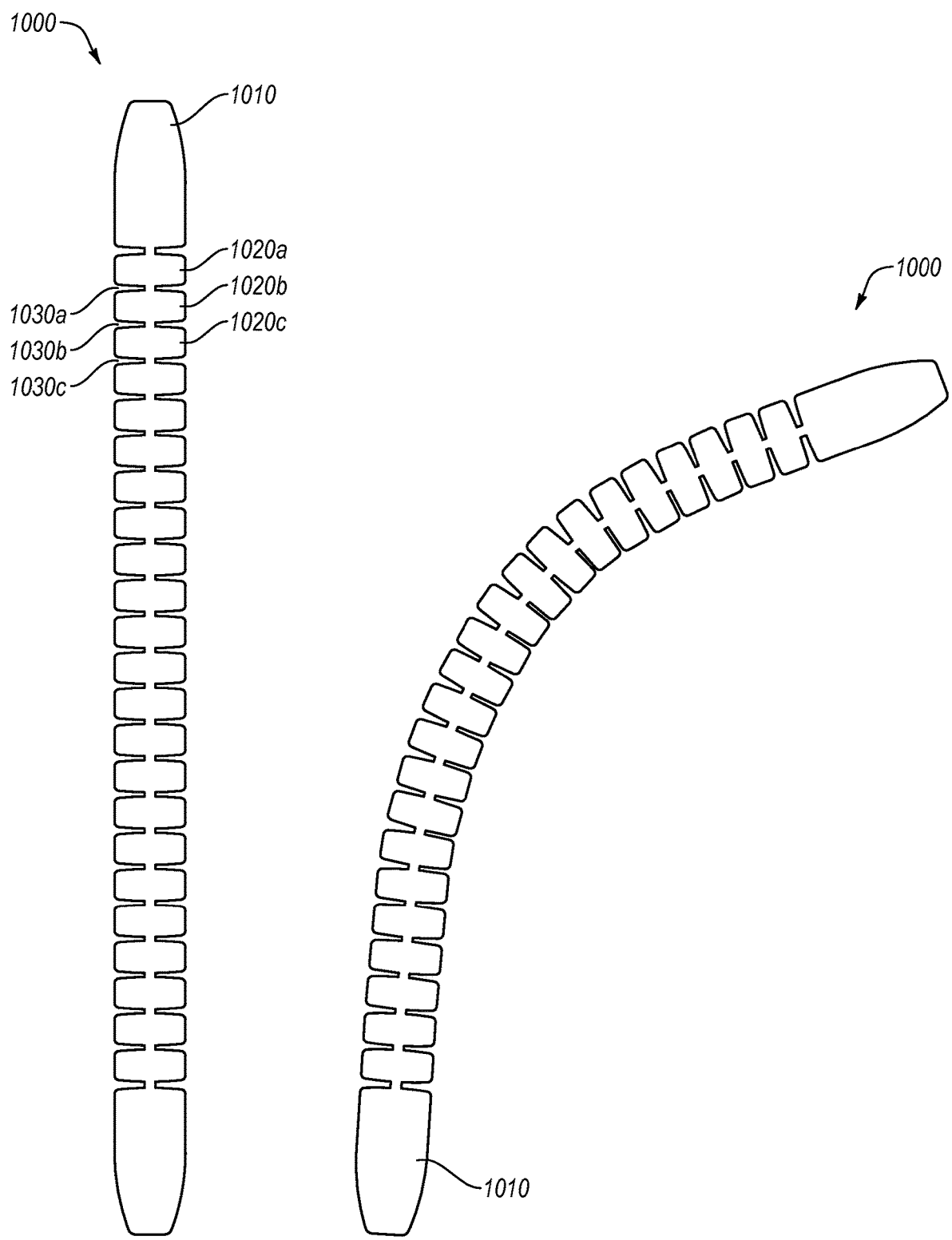
*Fig. 10A*  *Fig. 10B*

KINESIOLOGY TAPE

CROSS-REFERENCE TO RELATED APPLICATIONS

The present application claims priority to and the benefit of U.S. Provisional Patent Application Ser. No. 62/039,330, entitled KINESIOLOGY TAPE, which was filed on Aug. 19, 2014, and is hereby incorporated by reference in its entirety.

FIELD

This application is generally directed towards kinesiology tape and, in particular, kinesiology tape that may provide additional support.

BACKGROUND

Some physical injuries or physical ailments may require treatment or therapy that may benefit from physical support beyond that of a body of an individual. For example, leg, knee, torso, neck, shoulder, arm, or elbow injuries may require therapy or treatment that may use a brace, wrap, or other support. In addition, some sports or fitness activities may benefit from the use of a brace, wrap, or other support.

The subject matter claimed in the present disclosure is not limited to embodiments that solve any disadvantages or that operate only in environments such as those described above. Rather, this Background Section is provided to illustrate an example technology area where embodiments described in the present disclosure may be practiced.

SUMMARY

One or more embodiments of the present disclosure may include kinesiology tape that may include a first layer of fabric with an adhesive on a first side of the first layer of fabric. The kinesiology tape may also include a second layer of fabric that may be coupled to the first layer of fabric. The first layer of fabric and the second layer of fabric may form a receiving portion. The kinesiology tape may also include a support disposed in the receiving portion.

The object and advantages of the embodiments will be realized and achieved at least by the elements, features, and combinations particularly pointed out in the claims.

Both the foregoing general description and the following detailed description provide examples and are explanatory and are not restrictive.

BRIEF DESCRIPTION OF THE DRAWINGS

The appended drawings contain figures of one or more embodiments to further illustrate and clarify the present disclosure. Additionally, it will be appreciated that while the drawings may illustrate some sizes, scales, relationships, and configurations of the present disclosure, the drawings are not intended to limit the scope of the present disclosure. Example embodiments will be described and explained with additional specificity and detail through the use of the accompanying drawings in which:

FIG. 4 is a right-side view of an example embodiment of kinesiology tape with a receiving portion;

FIG. 5 is a left-side view of an example embodiment of kinesiology tape with a receiving portion;

FIG. 6 is a front view of an example embodiment of kinesiology tape with a receiving portion;

FIG. 7 is a rear view of an example embodiment of kinesiology tape with a receiving portion;

FIG. 10A is a front view of an example embodiment of a support;

FIG. 10B is a front view of an example embodiment of a support during motion;

DESCRIPTION OF EMBODIMENTS

Figure 1:
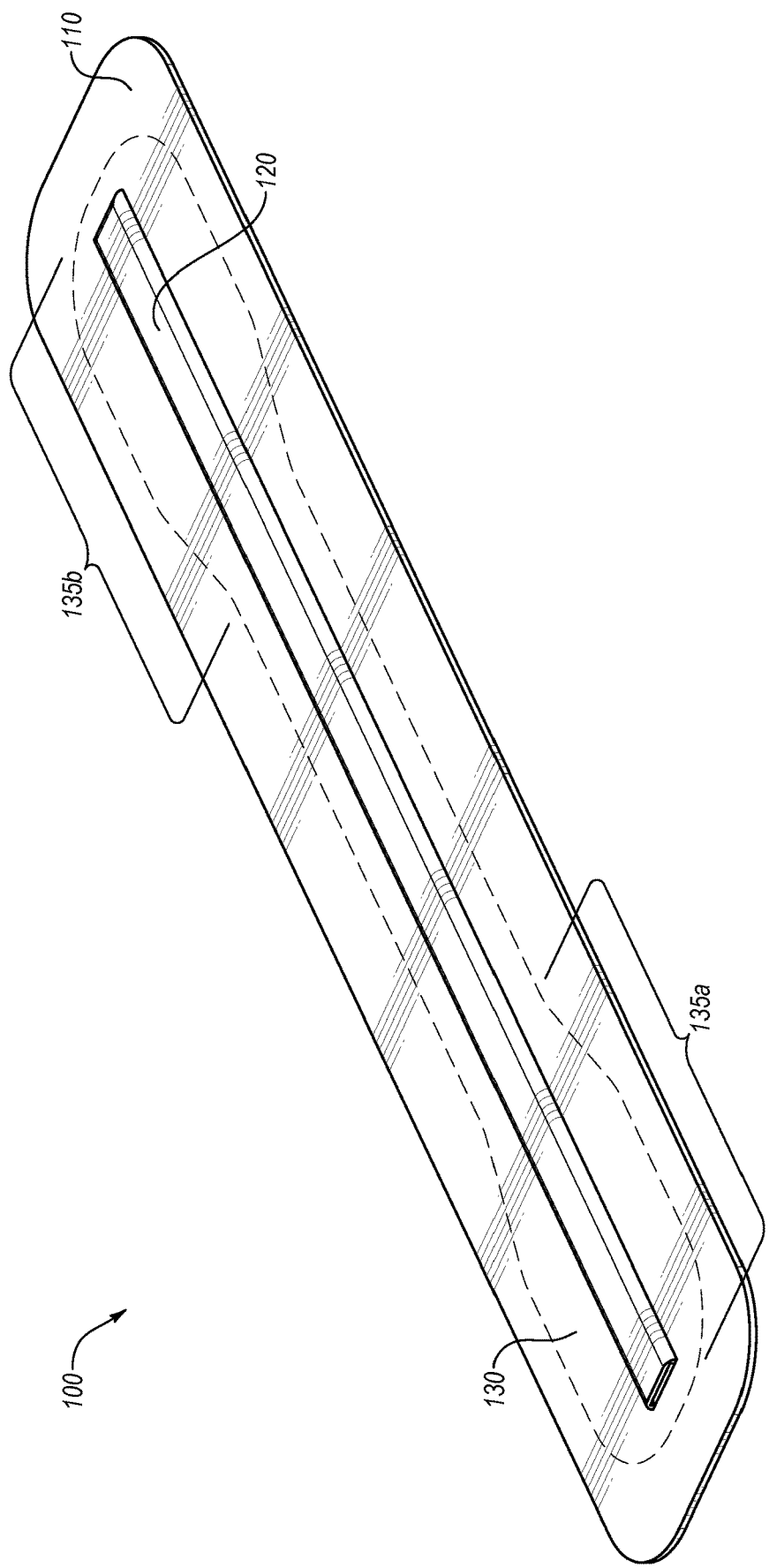
FIG. 1 is an upper perspective view of an example embodiment of kinesiology tape with a receiving portion.

One or more embodiments of the disclosure may relate to kinesiology tape and the kinesiology tape may include a support and/or a receiving portion to receive the support. The support may be removably disposed in the receiving portion or may be integrally disposed within the receiving portion. The support may be biased to facilitate motion in one plane while resisting motion in another plane. By using such a support, the kinesiology tape may provide additional physical support to a joint or body member. Additionally, such kinesiology tape may replace traditional braces or sleeves.

Kinesiology tape may be a thin tape with a non-adhesive side and an adhesive side that may be used in connection with sports and fitness. The adhesive may be a heat-activated acrylic and may be used to attach the kinesiology tape directly to the skin of a person. Kinesiology tape may have elasticity and pliability that generally mimic the skin, which may increase the comfort and facilitate use of the kinesiology tape. Kinesiology tape may be generally sweat, water, and weather resistant, which may allow for continued use over a period of several days.

Kinesiology tape may be useful in therapy to reduce soreness in overused and/or injured muscles and in rehabilitation to accelerate recovery. Kinesiology tape may have a lifting effect on the skin which may reduce swelling and inflammation by improving circulation and reduce pain by taking pressure off pain receptors.

In greater detail, kinesiology tape may be used for treating a variety of athletic injuries and physical ailments in an individual's legs, knees, torso, neck, shoulders, arms, elbows, and the like. Kinesiology tape may be frequently applied along soft tissue, such as muscles, ligaments, and tendons, to provide pain relief and a light, external support. Because kinesiology tape may not restrict motion and may have recoiling qualities, kinesiology tape may enable athletes and others to continue their activities while healing.

In particular, kinesiology tape may be elastic and stretchable in only one direction along an axis, which is typically along a length of the tape. The kinesiology tape may be stretched when it is applied to the skin and there may be a resulting tension in the tape that lifts the skin. The lifting of the skin may increase the space between the dermis and the muscle, which may increase blood flow and circulation of lymphatic fluid. This increased fluid flow may reduce swelling in injured areas. Lifting of the skin may also reduce pressure on swollen areas, particularly nociceptors, which may alleviate pain. Kinesiology tape may also provide some support and stability to injured areas. Additionally, kinesiology tape may create neuromuscular feedback which increases proprioception. Various taping techniques may have a tendency to either relax muscles or create stronger firing of muscles.

Kinesiology tape may be used in combination with icing, rest, stretching, massaging, and other remedies in order to relieve pain and to promote and speed up the body's natural healing process. Kinesiology tape generally may provide a greater freedom of movement and range of motion after application when compared to traditional athletic or surgical tapes, which are generally inelastic and wrapped around a joint for only stabilization and support. Traditional athletic and surgical tapes are used to apply compression to the portion of the body that is wrapped with the tape because the tape does not stretch in any direction. Kinesiology tape may eliminate the compression and restrictions associated with traditional athletic and surgical tapes.

Kinesiology tape may be used for longer periods of time than athletic or surgical tapes before removing and reapplying. For example, kinesiology tape may be made from cotton or synthetic fibers, and the tape may be breathable and waterproof, which may allow the tape to be worn over a period of several days. Some kinesiology tape may includes only a single layer or a small number of layers of fabric, and such tape may have a very small thickness and be lightweight. Its small thickness and light weight may allow such kinesiology tape to be used in a variety of configurations and may allow the kinesiology tape, for example, to be used under clothing.

Because kinesiology tape may be fabric, the kinesiology tape may be easily attached to the skin. In addition, the fabric may allow the tape to be contoured and shaped so that the kinesiology tape may be easily attached to various parts of the body. Kinesiology tape may also be used to support various portions of the body without the bulkiness and limited range of movement associated with traditional surgical and athletic tapes.

Braces may be used to support portions of the body. For example, knee braces and elbow braces are frequently used to provide additional support and/or stability to this portion of the body. Disadvantageously, braces are often large, bulky structures that require a large amount of space. In addition, braces typically encompass or surround the entire portion of the body to be supported. Furthermore, braces are often held in place by compression forces, which may limit circulation and blood-flow to that portion of the body. Additionally, many braces have large metal structures with exposed hinges that create pinch points. These metal structures are often elongated steel rods that are aligned and extend along a portion of the body such as an arm or leg. Many braces are heavy, unwieldy and may be configured to be used by people of certain sizes or particular portions of the body. Thus, braces of different shapes and sizes may be needed depending, for example, on the size of the person or the part of the body to which the brace is attached.

Sleeves may also be used to support portions of the body. For example, knee sleeves and elbow sleeves are frequently used to provide additional support to portions of the body. Disadvantageously, sleeves typically encompass or surround the entire portion of the body to be supported. Further, sleeves are often held in place by compression forces, which may limit circulation and blood-flow to that portion of the body. Additionally, many sleeves do not provide sufficient support for proper healing and tend to limit motion of the affected area. Furthermore, sleeves need to be repeatedly removed and cleaned during periods of prolonged use. Sleeves may be configured to be used by people of certain sizes or particular portions of the body. Thus, sleeves of different shapes and sizes may be needed depending, for example, on the size of the person or the part of the body to which the sleeve is attached.

A need therefore exists for kinesiology tape that eliminates the above-described disadvantages and problems.

FIG. 1 is an upper perspective view of an exemplary embodiment of kinesiology tape 100. The kinesiology tape 100 may include a first layer of fabric 110, a receiving portion 120, and a second layer of fabric 130. The first layer of fabric 110 and the second layer of fabric 130 may form the receiving portion 120. The receiving portion 120 may be shaped and/or configured to receive a support. The kinesiology tape 100 coupled with the support may be used by an individual. The kinesiology tape 100 may also have an adhesive on one side of the kinesiology tape 100.

The first layer of fabric 110 may include fabric made from cotton or synthetic fibers, and the first layer of fabric 110 may be breathable and waterproof, which may allow the kinesiology tape 100 to be worn over a period of several days. In these and some embodiments, the first layer of fabric 110 may be made of viscose fiber for warp threads and weft threads. In some embodiments, the first layer of fabric 110 may include viscose fiber for warp threads and polyethylene terephthalate ("PET") fiber for weft threads. These are merely examples and any combination of materials may be used for the materials of the first layer of fabric 110 for either the warp thread or the weft thread. Additionally or alternatively, any type of textile or other fabric may be used and any type of fiber, filament, polymer, or thread may be used to form the fabric.

In some embodiments, the first layer of fabric 110 may have properties of elasticity in a first axis and inelasticity in a second axis. For example, the first layer of fabric 110 may be elastic longitudinally along the length of the kinesiology tape 100, but may be inelastic along the width of the of the kinesiology tape 100. In some embodiments, the kinesiology tape 100 may stretch along one axis, such as longitudinally, and may or may not stretch in other axes.

The second layer of fabric 130 may be made of materials and may have properties similar to the description of the first layer of fabric 110. The first layer of fabric 110 and the second layer of fabric 130 may be made of different materials. By way of non-limiting example, the first layer of fabric 110 may be made of viscose fibers and the second layer of fabric 130 may be made of viscose fibers for warp threads and PET fibers for weft threads.

In some embodiments, the second layer of fabric 130 may include one or more wings, such as wings 135*a* and 135*b*. The wings 135*a* and 135*b* may be used to provide additional stability between the first layer of fabric 110 and the second layer of fabric 130. For example, when using the kinesiology tape 100 such that the kinesiology tape 100 may flex longitudinally in a plane generally parallel with the first layer of fabric 110, the wings 135*a* and 135*b* may provide greater surface area or regions of coupling between the first layer of fabric 110 and the second layer of fabric 130 at the portions of the kinesiology tape 100 undergoing the most displacement.

The second layer of fabric 130 may be coupled with the first layer of fabric 110. The coupling may include any method or process by which the first layer of fabric 110 and the second layer of fabric 130 may be coupled, either permanently or removably. For example, coupling may include using an adhesive to attach the first layer of fabric 110 and the second layer of fabric 130, interweaving fibers of the first layer of fabric 110 with fibers of the second layer of fabric 130, melting the first layer of fabric 110 and the second layer of fabric 130 together, sewing the first layer of fabric chemically bonding the first layer of fabric 110 and the second layer of fabric 130 together, sonically welding the first layer of fabric 110 and the second layer of fabric together, etc. The first layer of fabric 110 and the second layer of fabric 130 may form a receiving portion 120 when coupled together.

The receiving portion 120 may be sized, shaped, or otherwise configured to receive one or more supports. The receiving portion 120 may be a pocket, pouch, or any other type of receiving portion. In some embodiments, there may be multiple receiving portions. In some embodiments, the receiving portion 120 may be aligned longitudinally along a length of the kinesiology tape 100 and/or laterally across a width of the kinesiology tape 100. In some embodiments, each side of the receiving portion 120 may be open, closed, and/or closeable. For example, the receiving portion 120 may have adhesive portions to close the receiving portion 120 after the support is inserted. It will be appreciated that receiving portion 120 may be closed by other structures or means such as fasteners, clasps, snaps, buttons, the force applied when the kinesiology tape 100 is stretched and placed on the skin, etc. In these and other embodiments, the one or more supports may be used multiple times.

In some embodiments, the receiving portion 120 may be aligned longitudinally along the length of the kinesiology tape 100. Alternatively or additionally, the receiving portion 120 may be disposed at angles along the kinesiology tape 100, for example, about 30°, 45°, 60°, 90°, etc. The receiving portion 120 may also be disposed at other angles, including angles that are larger and/or smaller than the examples provided.

In some embodiments, the one or more supports may be aligned in a particular manner with the kinesiology tape 100. For example, in some embodiments the kinesiology tape 100 may have properties of elasticity in one axis and the one or more supports may be generally aligned in the direction of that axis (e.g. longitudinally). The one or more supports may also be disposed at an angle to which the kinesiology tape 100 may have properties of elasticity, such as an angle of about 30°, 45°, 60° or 90°. It will be appreciated the one or more supports may be disposed at various angles depending, for example, upon the intended use of the kinesiology tape 100 and/or the one or more supports.

In some embodiments, the receiving portion 120 may be sized and/or configured to receive one or more supports and/or supports of different sizes and configurations. Such a sizing and/or configuration may allow, for example, multiple supports to be disposed in a single receiving portion and may provide increased support, rigidity, and the like. Such a sizing and/or configuration may also allow the kinesiology tape 100 and/or supports to be customized for particular uses and/or configurations. For instance, if a certain degree of support is desired, then one support may be placed in the receiving portion 120. If additional support is desired, then two or more supports may be placed in the receiving portion 120.

In some embodiments, the kinesiology tape 100 may include an adhesive on one side. For example, the adhesive may be disposed on the first layer of fabric 110 on the side opposite the second layer of fabric 130, or may be disposed on the first layer of fabric 110 on the same side as the second layer of fabric 130. The adhesive may also be disposed on the second layer of fabric 130. The kinesiology tape 100 may also include backing to protect and/or prevent the adhesive from being exposed before use that may be removed to expose the adhesive for application of the kinesiology tape 100. For example, the backing may include a coated paper or other material which may resist adhesion from the adhesive on at least one side. The backing may be vinyl, laminate, plastic, polymer, or any other material that may prevent the adhesive from bonding before a desired application of the kinesiology tape 100.

In some embodiments, the kinesiology tape 100 may include one or more supports that may be integrally formed as part of a unitary, one-piece structure. That is, the supports may be part of the kinesiology tape 100 and/or permanently attached to the kinesiology tape 100. The supports can also be interchangeable, replaceable, and/or removably attached to the kinesiology tape 100 when desired. This may allow the kinesiology tape 100 to be used without a support and may allow the supports to be interchangeably attached to the kinesiology tape 100 so that the support, for example, may be specifically tailored to the activity being conducted. For example, if a strenuous activity is being conducted, then a specific type of support may be used in connection with the kinesiology tape 100. On the other hand, if a less strenuous activity is being performed, then a different type of support or no support may be used. Advantageously, if the supports can be interchangeably connected to the kinesiology tape 100, then the supports may be readily changed. This may also allow one or a limited number of supports to be used with many different pieces or strips of kinesiology tape.

In some embodiments, the include kinesiology tape 100 may be applied directly to an affected area of an individual without covering or encompassing the entire affected area. In addition, the kinesiology tape 100 may be applied directly to the body of the individual, and the kinesiology tape 100 and the support may remain in the place where the kinesiology tape 100 is applied. This may give the individual greater control over where the support is located, which may result in improved accuracy and precision in placement of the support. In addition, because the kinesiology tape 100 and support may not cover or encompass all or a portion the affected area, the kinesiology tape 100 and support may be easier to use.

In some embodiments, the kinesiology tape 100 may be used in a manner similar to a conventional brace or sleeve. Advantageously, because the kinesiology tape 100 may not provide compressive forces on the affected area and the kinesiology tape 100 may not surround or encompass the affected area, the kinesiology tape 100 may allow increased circulation and fluid flow in comparison to a traditional brace or sleeve. Further, because the support may be disposed adjacent or at least proximate the skin, the support may be smaller than a conventional brace or sleeve. Additionally, the kinesiology tape 100 may be much smaller, more compact and easier to use than a conventional brace or sleeve.

Additions, omissions, and/or other modifications may be made to the kinesiology tape 100 of FIG. 1 without departing from the scope of the present disclosure. For example, there may be multiple receiving portions and/or multiple supports. As another example, the kinesiology tape 100 may include only a single layer of fabric to which the support may be affixed, rather than using two or more layers of fabric to create a receiving portion.

Figure 2:
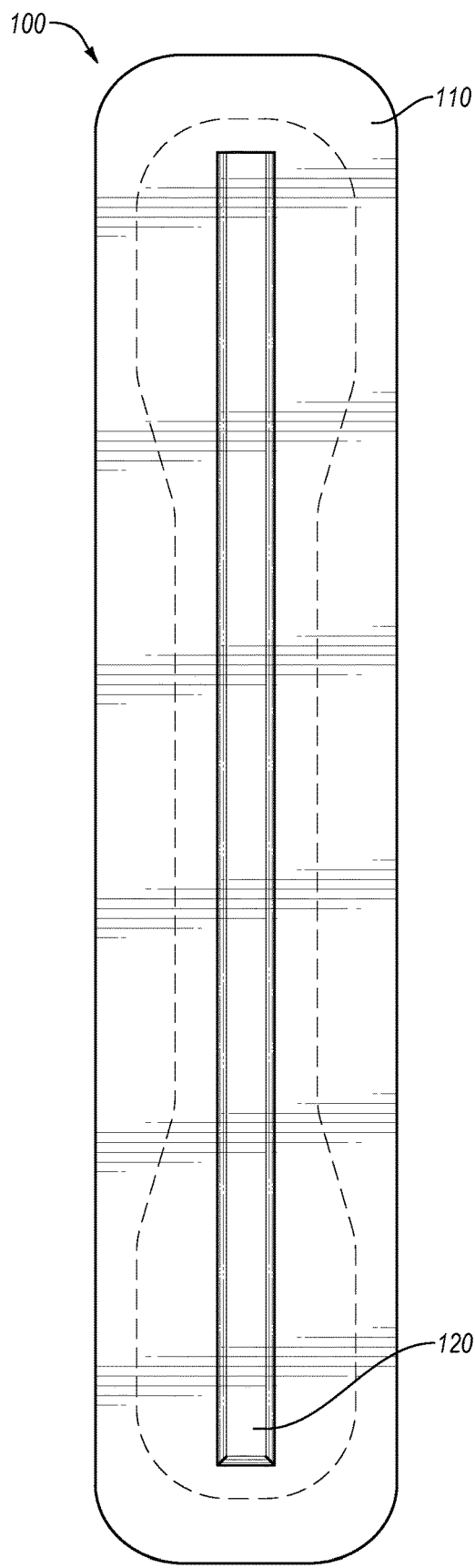
FIG. 2 is a top view of an example embodiment kinesiology tape with a receiving portion.

FIG. 2 is a top view of an exemplary embodiment of kinesiology tape 100 with a receiving portion 120. The kinesiology tape 100 may include a first layer of fabric 110 and a receiving portion 120. The kinesiology tape 100 may be similar or identical to the kinesiology tape 100 of FIG. 1, and may serve to illustrate an alternative view of the kinesiology tape 100 of FIG. 1 to facilitate an understanding of the present disclosure.

Figure 3:
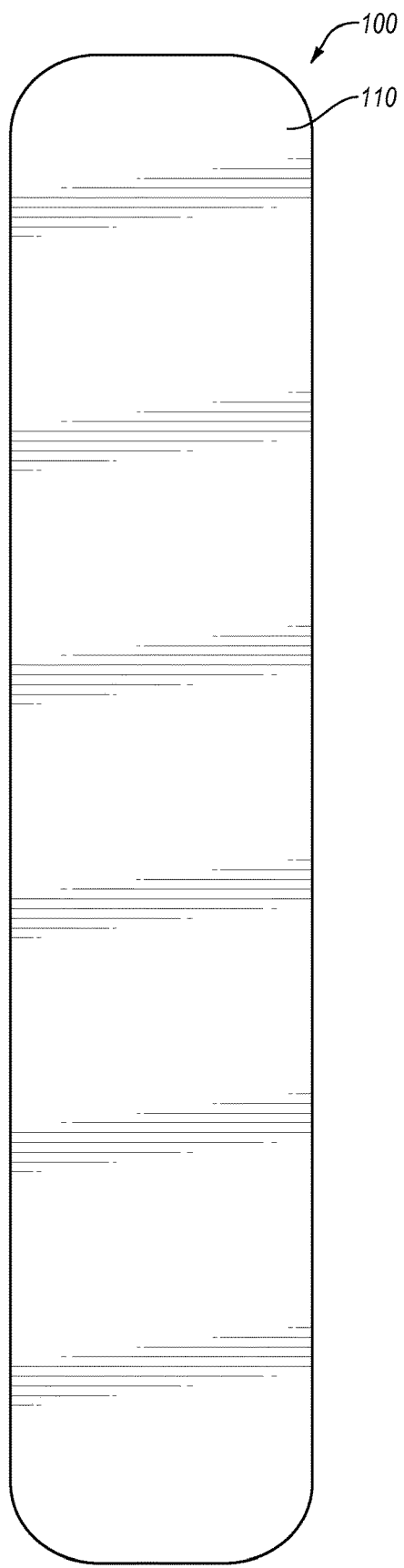
FIG. 3 is a bottom view of an example embodiment of kinesiology tape.

FIG. 3 is a bottom view of an exemplary embodiment of kinesiology tape 100. The kinesiology tape 100 may include a first layer of fabric 110. The kinesiology tape 100 may be similar or identical to the kinesiology tape 100 of FIG. 1, and may serve to illustrate an alternative view of the kinesiology tape 100 of FIG. 1 to facilitate an understanding of the present disclosure.

FIG. 4 is a right-side view of an an exemplary of kinesiology tape 100 with a receiving portion 120. The kinesiology tape 100 may include a first layer of fabric 110 and a receiving portion 120. The kinesiology tape 100 may be similar or identical to the kinesiology tape 100 of FIG. 1, and may serve to illustrate an alternative view of the kinesiology tape 100 of FIG. 1 to facilitate an understanding of the present disclosure.

FIG. 5 is a left-side view of an exemplary embodiment of kinesiology tape 100 with a receiving portion 120. The kinesiology tape 100 may include a first layer of fabric 110 and a receiving portion 120. The kinesiology tape 100 may be similar or identical to the kinesiology tape 100 of FIG. 1, and may serve to illustrate an alternative view of the kinesiology tape 100 of FIG. 1 to facilitate an understanding of the present disclosure.

FIG. 6 is a front view of an exemplary embodiment of kinesiology tape 100 with a receiving portion 120. The kinesiology tape 100 may include a first layer of fabric 110 and a receiving portion 120. The kinesiology tape 100 may be similar or identical to the kinesiology tape 100 of FIG. 1, and may serve to illustrate an alternative view of the kinesiology tape 100 of FIG. 1 to facilitate an understanding of the present disclosure.

FIG. 7 is a rear view of an exemplary embodiment of kinesiology tape 100 with a receiving portion 120. The kinesiology tape 100 may include a first layer of fabric 110 and a receiving portion 120. The kinesiology tape 100 may be similar or identical to the kinesiology tape 100 of FIG. 1, and may serve to illustrate an alternative view of the kinesiology tape 100 of FIG. 1 to facilitate an understanding of the present disclosure.

Figure 8:
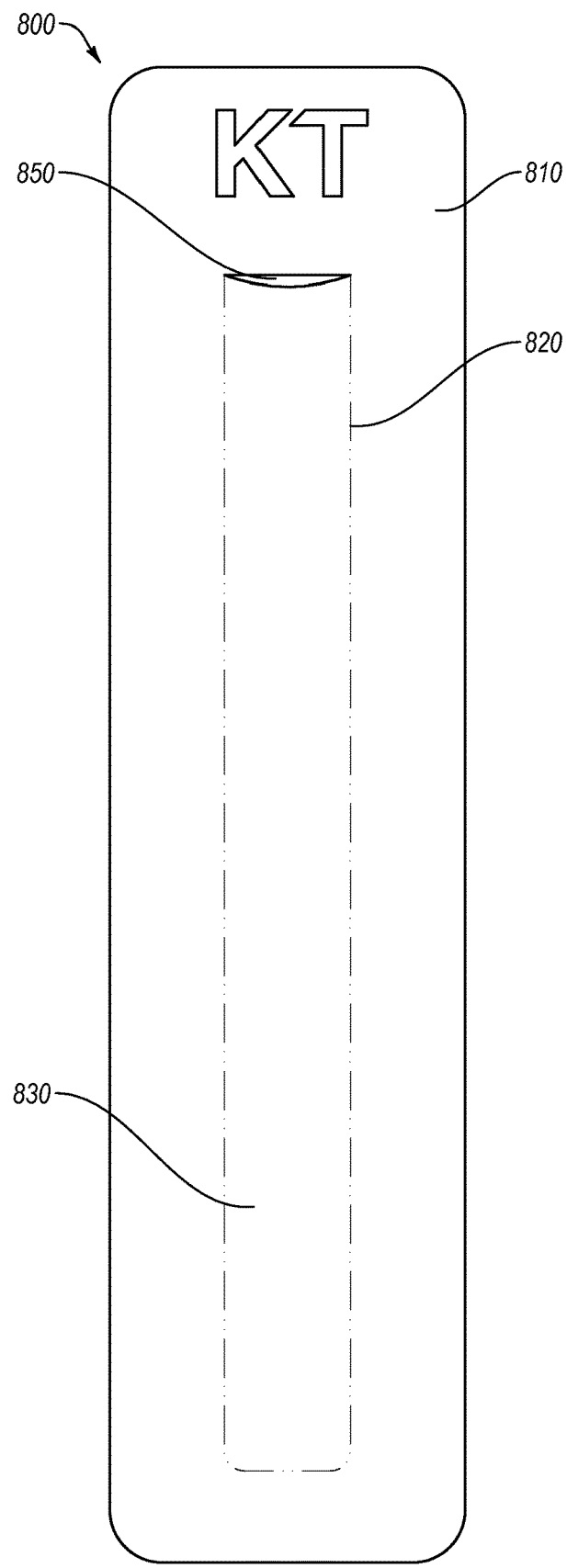
FIG. 8 is a front view of another example embodiment of kinesiology tape with a receiving portion.

FIG. 8 is a front view of another an exemplary of kinesiology tape 800 with a receiving portion 820. The kinesiology tape 800 may include an opening 850 to the receiving portion 820. The opening 850 may be of any shape, size, and/or configuration to facilitate a support being removably disposed within the receiving portion 820. For example, opening 850 may be sized and/or positioned such that a support may be slid into the receiving portion 820. As described above, in some embodiments the opening 850 may be closable or sealed.

In some embodiments, the opening 850 may be at one end or both ends of the receiving portion 820. In some embodiments, the opening 850 may not be at either end of the receiving portion 820, but instead may be located some distance down the receiving portion 850, such as about one fourth, one half, or one third of the length of the pocket. The opening 850 may be at any angle relative to the receiving portion 820, such as about 0°, 30°, 45°, 60°, or 90°. The opening 850 may not extend across the entire receiving portion 820. The support and/or the receiving portion 820 may be flexed to insert the support into the receiving portion 820.

Additions, omissions, and/or other modifications may be made to the kinesiology tape 800 of FIG. 8 without departing from the scope of the present disclosure. For example, there may be multiple receiving portions 820 and/or multiple supports. As another example, the kinesiology tape 800 may include only a single layer of fabric to which the support may be affixed, rather than using two or more layers of fabric to create a receiving portion. As an additional example, in some embodiments the opening 850 may be omitted and the support may be part of a unitary, one-piece structure.

Figure 9:
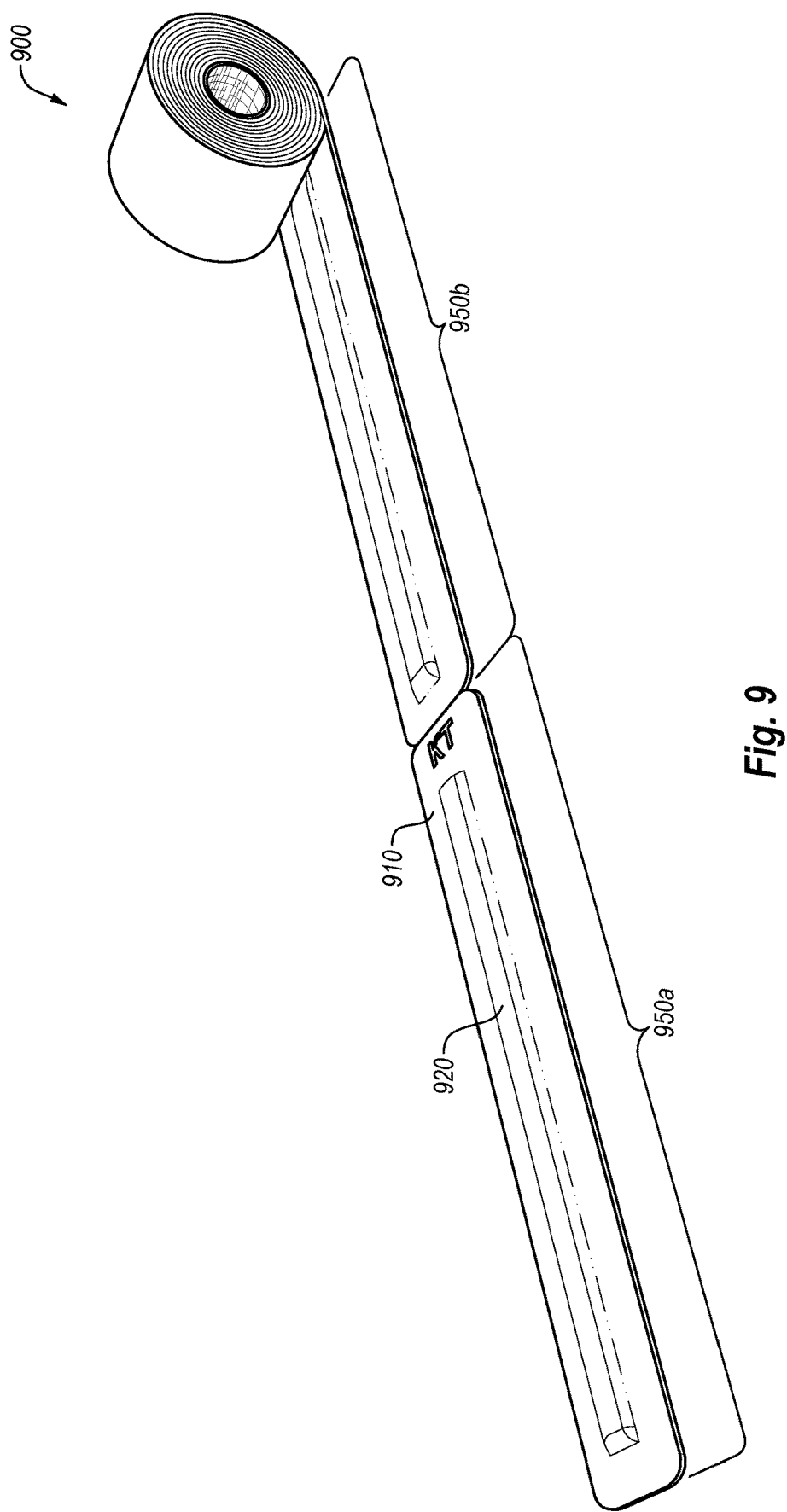
FIG. 9 is an isometric view of an example embodiment of a roll of kinesiology tape.

FIG. 9 is an isometric view of an exemplary embodiment of a roll of kinesiology tape 900. The roll of kinesiology tape 900 may include one or more application portions, such as application portions 950a and 950b. While application portions 950a and 950b may be described, it will be appreciated that such a description may also be applicable to any application portions and/or the entire roll of kinesiology tape 900.

Each application portion 950a and/or 950b may be similar to the kinesiology tape 100 of FIG. 1 and/or the kinesiology tape 800 of FIG. 8. For example, the application portion 950a may include a first layer of fabric 910 and a receiving portion 920. The first layer of fabric 910 may be similar to the first layer of fabric 110 of FIG. 1 and/or the first layer of fabric 810 of FIG. 8. The receiving portion 920 be similar to the receiving portion 120 of FIG. 1 and/or the receiving portion 820 of FIG. 8.

In some embodiments, the roll of kinesiology tape 900 may be completely cut or partially cut between of the application portions 950a and 950b. For example, the roll of kinesiology tape 900 may be cut from a single weave or length of fabric and the threads connecting the application portions 950a and 950b may be cut. Additionally or alternatively, only a portion of the threads may be cut or the threads may be perforated.

In some embodiments, the roll of kinesiology tape 900 may include an adhesive to attach the application portion 950a and/or 950b to an individual using the kinesiology tape 900. Any adhesive for attaching the application portion 950a and/or 950b to the individual may be used. For example, a heat-activated acrylic adhesive may be used. In some embodiments, the roll of kinesiology tape 900 may have a backing to prevent the kinesiology tape 900 from adhering prior to a desired use. For example, the backing may protect or otherwise prevent exposure of the adhesive until use of the application portion 950a and/or 950b. The backing may be similar to the backing described with reference to FIG. 1.

In some embodiments, the backing of the roll of kinesiology tape 900 may be uncut or unbroken for the entire length of the roll of kinesiology tape 900. The backing may be uncut even if the roll of kinesiology tape 900 may be cut or partially cut between application portions 950a and 950b. For example, the threads of fabric between the application portions 950a and 950b may be cut while the backing may be uncut. Additionally or alternatively, the backing may be partially cut, perforated, or otherwise weakened to facilitate tearing, ripping, breaking, cutting, etc. at the juncture between the application portions 950a and 950b.

Additions, omissions, and/or other modifications may be made to the roll of kinesiology tape 900 of FIG. 9 without departing from the scope of the present disclosure. For example, the roll of kinesiology tape 900 may include only one application portion or many application portions. As another example, any of the application portions may include multiple receiving portions and/or multiple supports. As an additional example, any of the application portions may include only a single layer of fabric to which the support may be affixed, rather than using two or more layers of fabric to create a receiving portion. As an additional example, any of the application portions may include the support as part of a unitary, one-piece structure. In these and other embodiments, the roll of kinesiology tape 900 may be configured as a square or rectangle with a side approximately the length of the support and/or the length of the application portion.

FIG. 10A is a front view of an exemplary embodiment of a support or stay 1000. The support 1000 may include an end 1010, one or more teeth, teeth 1020a, 1020b, and 1020c. The support 1000 may also include one or more voids 1030, such as voids 1030a, 1030b, and 1030c. The support 1000 may include a ridge or spine attaching the teeth 1020.

In some embodiments, the support 1000 may be biased to support motion in one plane or direction and/or to resist motion in another direction and/or plane. The teeth 1020 and/or the voids 1030 may be configured, shaped, and/or sized to facilitate motion in one direction or plane while limiting or resisting motion in another direction and/or plane. For example, the support 1000 may flex, rotate, or otherwise move in a plane that is generally parallel with a front face of the support 1000. For example, as the support 1000 rotates in this plane, the teeth 1020 may move closer together through the voids 1030, creating a curvature or flexion motion in that plane. Additionally or alternatively, the spine or ridge to which the teeth 1020 attach may resist motion in a plane perpendicular to that plane, for example, a plane perpendicular to the front face of the support 1000. In some embodiments, the plane in which motion is facilitated may be a plane of natural motion of a joint and the plane in which motion is resisted may be a plane that is an unnatural motion of the joint. An example of the facilitation and resistance of motion may be described in greater detail with reference to FIG. 13.

In some embodiments, the end 1010 may be pointed, tapered, or otherwise shaped or formed to facilitate entry of the support 1000 into a receiving portion. Additionally or alternatively, the end 1010 may be shaped of formed to resist exit from a receiving portion. For example, the end 1010 may be bulbous, barbed, hooked, or otherwise have features to resist withdrawal of the support 1000 from a receiving portion.

FIG. 10B is a front view of an example embodiment of a support 1000 during motion. For example, FIG. 10B may be an example of the support 1000 of FIG. 10A during motion. As described above the teeth 1020 and/or the voids 1030 of the support 1000 may facilitate motion in a plane generally parallel with a front face of the support 1000, and the illustration of FIG. 10B may illustrate such motion.

In some embodiments, the support 1000 may be generally planar, elongated, thin, and flat. The support 1000 may generally have a length equal to the length or substantially equal to the length of a receiving portion. In some embodiments, the support 1000 may be configured to have different amounts of strength, rigidity, etc. For example, using different materials, different spacing and/or configurations of teeth 1020 and/or voids 1030, different thickness of the ridge or spine, etc. may cause the support 1000 to have different amounts of strength, rigidity, etc. Thus, depending upon the intended use of kinesiology tape, supports with different features and characteristics may be used. Using supports with different characteristics may allow, for instance, a support with relatively low rigidity and stiffness to be used to provide a first level of support. A support with a larger degree of rigidity and stiffness may be used to provide a second level of support. This may allow different portions of the body to have different levels of support. This may also allow different levels of support to be provided to the same portion of the body. Any number of types of supports and levels of support may be used for the same and/or different portions of the body.

In some embodiments, the support 1000 may be constructed from plastic, metal, composites, etc. The support 1000 may have different shapes, sizes, configurations, and arrangements depending upon the intended use of the kinesiology tape. For example, the supports may have different lengths and/or widths, depending on the needs of the particular individual. The support 1000 may also have different flexibility, elasticity, resiliency etc., which may allow individuals to customize the healing process to suit their needs. In addition, the support 1000 may be flexible to allow the support 1000 to bend with kinesiology tape as applied to a body or object.

Additions, omissions, and/or other modifications may be made to the support 1000 of FIGS. 10A and 10B without departing from the scope of the present disclosure. For example, the support 1000 may be constructed without the teeth 1020 and/or the voids 1030. As another example, the support may have different dimensions than those illustrated.

Figures 11A, 11B:
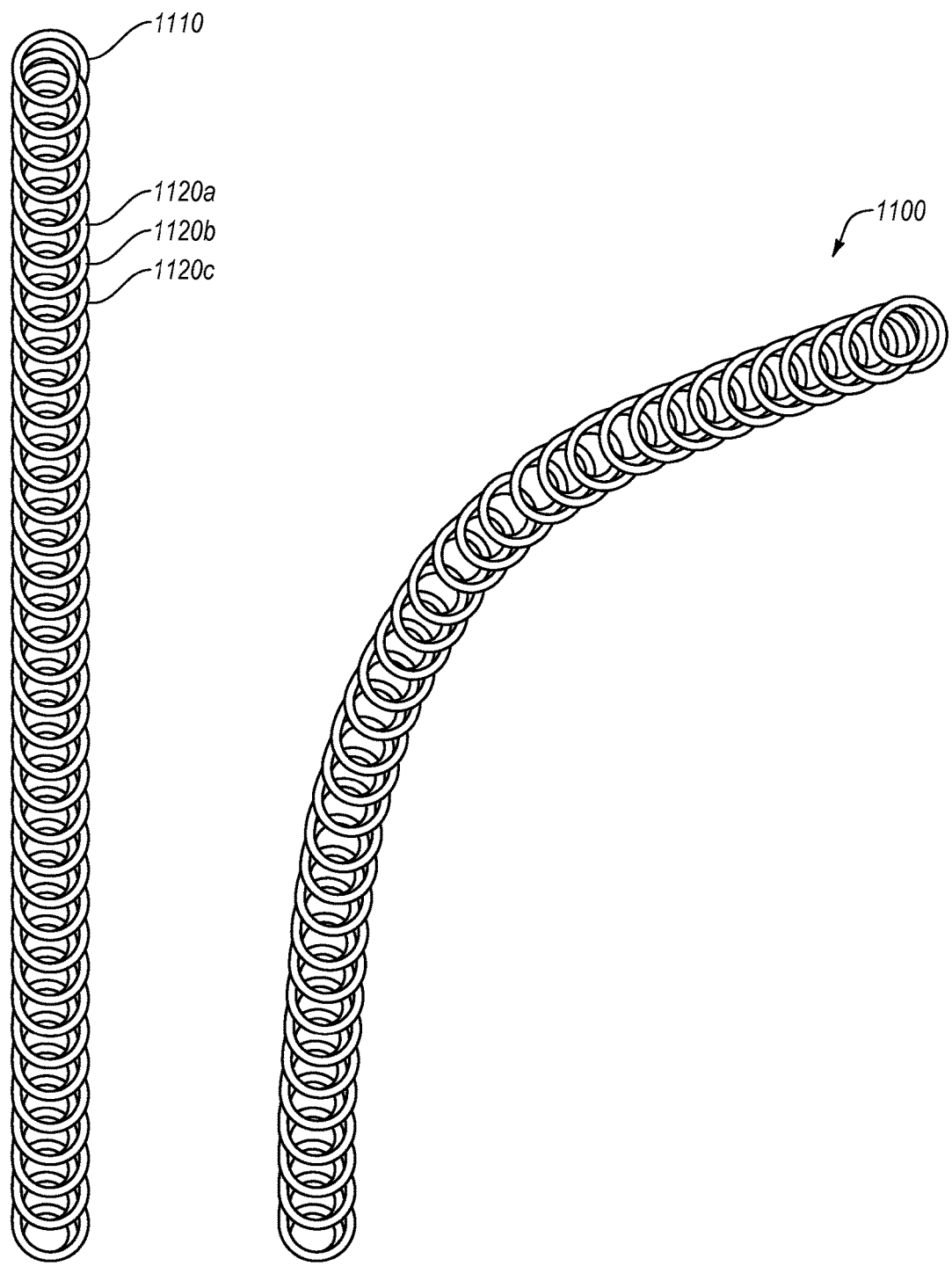
FIG. 11A is a front view of another example embodiment of a support.
FIG. 11B is a front view of another example embodiment of a support during motion.

FIG. 11A is a front view of another example embodiment of a support 1100. The support 1100 may include an end 1110 and one or more links 1120, such as links 1120a, 1120b, and 1120c. The support 1100 may be similar in description to the support 1000 of FIGS. 10A and 10B. For example, the support 1100 may be made of similar materials, serve similar purposes, resist and/or facilitate motion in similar planes, be used in similar ways, etc. FIG. 11A may serve to illustrate the breadth of the present disclosure by showing alternative embodiments of a support in accordance with the present disclosure.

In some embodiments, the end 1110 may be a terminal link and/or may be a differently shaped link. For example, the end 1110 may serve a similar purpose or function to the end 1010 of the support 1000 of FIGS. 10A and 10B.

The links 1120a, 1120b, and 1120c may be links of a coil, spring, chain, or similar device. The links 1120a, 1120b, and 1120c may be interlocking, interwoven, or otherwise connected to each other. In some embodiments, the form of connection that the links 1120a, 1120b, and 1120c may use may be based on a use of the support 1100. For example, the links 1120a, 1120b, and 1120c may be thicker and closer together to provide greater support, and may be spaced further apart and may be thinner to provide less support. Additionally or alternatively, the links 1120a, 1120b, and 1120c may be shaped, spaced, sized, and/or configured to facilitate motion in one plane. The links 1120a, 1120b, and 1120c may also be shaped, spaced, sized, and or configured to resist motion in another plane. For example, the links 1120a, 1120b, and 1120c may facilitate motion in a plane generally parallel with a front face of the support 1100. As another example, the links 1120a, 1120b, and 1120c may resist motion in another plane perpendicular to the front face of the support 1100. While the links 1120a, 1120b, and 1120c have been described, it will be appreciated that any number of links of the support 1100 may also comply with the description of the present disclosure. Additionally or alternatively, only one link or two links of the support 1100 may function, operate, etc. as described in the present disclosure.

In some embodiments, the support 1100 may reduce or remove pressure on a joint. For example, the support 1100 may be configured as a spring and used with kinesiology tape and positioned on an individual such that the spring absorbs some or all of the load of a joint.

FIG. 11B is a front view of an exemplary embodiment of a support 1200 during motion. For example, FIG. 11B may be an example of the support 1100 of FIG. 11A during motion. As described above the links 1120a, 1120b, and 1120c of the support 1100 may facilitate motion in a plane generally parallel with a front face of the support 1100, and the illustration of FIG. 11B may illustrate such motion. While motion in the plane generally parallel with the front face of the support 1100 may be illustrated, motion in any plane of any number of planes may be facilitated and/or resisted. In some embodiments, multiple planes of facilitating motion and/or resisting motion may be accomplished using multiple supports.

Additions, omissions, and/or other modifications may be made to the support 1100 of FIGS. 11A and 11B without departing from the scope of the present disclosure. For example, the support 1100 may be constructed only partially of links 1120 and other materials for other portions of the support 1100. As another example, the support may have different dimensions than those illustrated.

Figure 12:
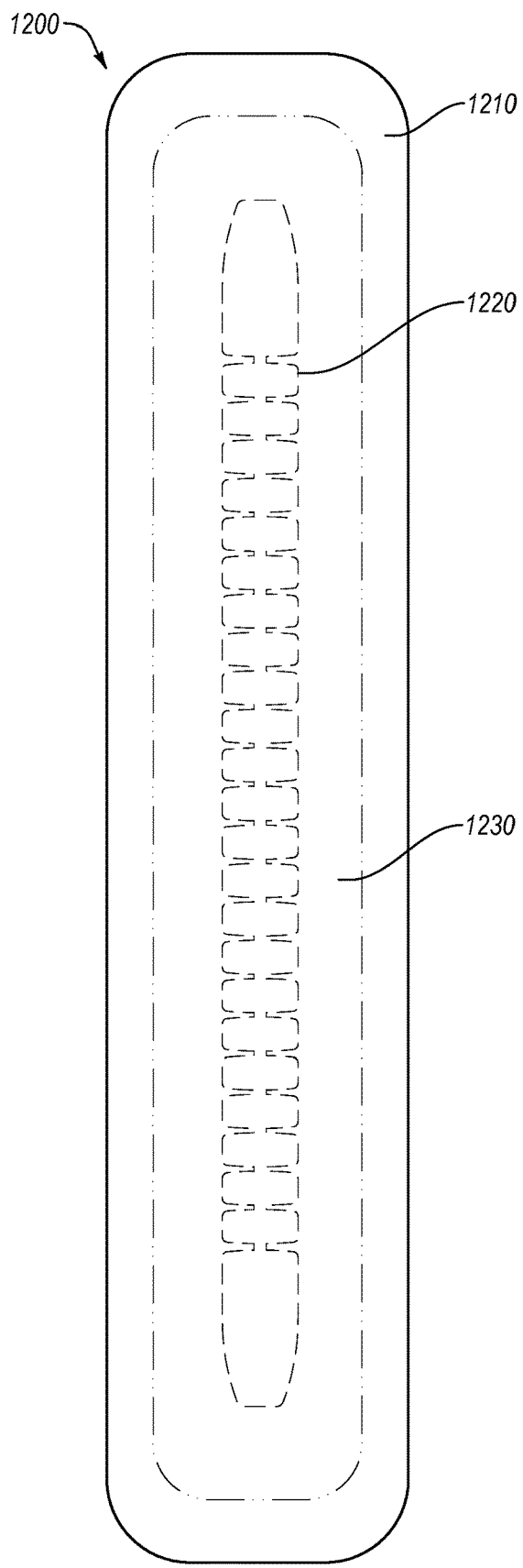
FIG. 12 is a front view of an example embodiment of kinesiology tape with a support.

FIG. 12 is a front view of an example embodiment of kinesiology tape 1200 with a support 1220. The kinesiology tape 1200 may include a first layer of fabric 1210 and a second layer of fabric 1230 forming a receiving portion. The first layer of fabric 1210 and the second layer of fabric 1230 may be similar to the first layer of fabric 110 and the second layer of fabric 130 of FIG. 1 and/or the first layer of fabric 810 and the second layer of fabric 830 of FIG. 8. The support 1220 may be similar to the support 1000 of FIG. 10 and/or the support 1100 of FIG. 11. The kinesiology tape 1200 may also include an adhesive and/or backing as described with respect to FIG. 1.

In some embodiments, the support 1220 may be affixed between the first layer of fabric 1210 and the second layer of fabric 1230. For example, the first layer of fabric 1210 and the second layer of fabric 1230 may be coupled using an adhesive, interwoven, melted, chemically bonded, sewn, sonically welded, etc. completely around the support 1220 such that the support 1220 may be completely enclosed between the first layer of fabric 1210 and the second layer of fabric 1230.

In some embodiments, the kinesiology tape 1200 may be packaged with a plurality of individual strips of the kinesiology tape 1200. The plurality of individual strips may include backing, with separate backing for each of the individual strips of the kinesiology tape 1200. In some embodiments, the plurality of individual strips of the kinesiology tape 1200 may include a common, continuous sheet of backing that may be completely unbroken or uncut or may be partially cut, perforated, or otherwise weakened.

In some embodiments, an additional layer of material may be included to maintain the support 1220 in a particular location and/or orientation with respect to the first layer of fabric 1210. Additionally or alternatively, the support 1220 may include features such as hooks, barbs, hook and loop fasteners such as VELCRO®, or other devices to resist movement relative to the first layer of fabric 1210.

Additions, omissions, and/or other modifications may be made to the kinesiology tape 1200 of FIG. 12 without departing from the scope of the present disclosure. For example, there may be multiple receiving portions and/or multiple supports. As another example, the kinesiology tape 1200 may include only a single layer of fabric to which the support may be affixed, rather than using two or more layers of fabric to create a receiving portion.

Figure 13:
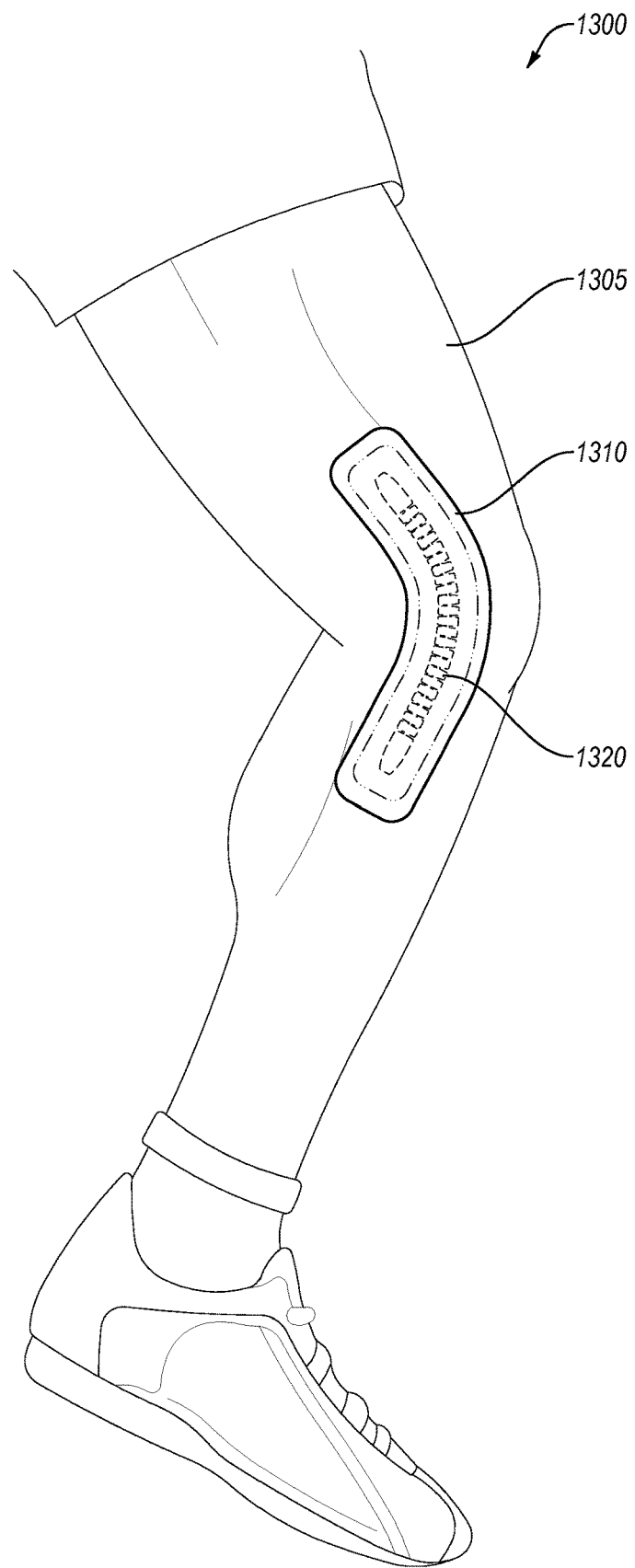
FIG. 13 is an elevation view of an example embodiment of kinesiology tape with a support attached to a leg of an individual.

FIG. 13 is an elevation view of an example embodiment of kinesiology tape 1300 with a first layer of fabric 1310 and a support 1320 attached to a leg 1305 of an individual. The first layer of fabric 1310 and the support 1320 may be similar to the first layer of fabric 110 of FIG. 1, the first layer of fabric 810 of FIG. 8, and/or the first layer of fabric 1210 of FIG. 12. The support 1320 may be similar to the support 1000 of FIG. 10, the support 1100 of FIG. 11, and/or the support 1220 of FIG. 12. The kinesiology tape 1300 may also include an adhesive and/or backing as described with respect to FIG. 1.

In some embodiments, the kinesiology tape 1300 may be applied to an individual. For convenience in describing an example, FIG. 13 illustrates the kinesiology tape 1300 being applied to the leg 1305 of an individual, but any number of portions of kinesiology tape 1300 may be applied to any portion or portions of the body of an individual.

In some embodiments, the kinesiology tape 1300 may have an integral support (such as that illustrated in FIG. 12) and may be applied directly to the leg 1305 as desired. Applying the kinesiology tape 1300 may include determining a particular desired orientation of the kinesiology tape 1300.

In some embodiments, the kinesiology tape 1300 may include removable supports, and the removable supports may be inserted prior to application of the kinesiology tape 1300 to the leg 1305. In these and other embodiments, for example when an opening of a receiving portion may not be at either end of the receiving portion, the support 1320 and/or the kinesiology tape 1300 may be flexed in order to insert the support 1320 into the receiving portion of the kinesiology tape 1300. To apply the kinesiology tape 1300 to the leg 1305, the backing of the kinesiology tape 1300 may be removed, exposing an adhesive. The kinesiology tape 1300 with the support may then be applied as desired to the leg 1305. Alternately or additionally, the kinesiology tape 1300 may be applied to the leg 1305 by removing the backing of the kinesiology tape 1305 and exposing the adhesive prior to inserting the support 1320 into the receiving portion.

Additions, omissions, and/or other modifications may be made to the kinesiology tape 1300 of FIG. 13 without departing from the scope of the present disclosure. For example, there may be multiple receiving portions and/or multiple supports. As another example, the kinesiology tape 1300 may include only a single layer of fabric to which the support may be affixed, rather than using two or more layers of fabric to create a receiving portion. As an additional example, the support 1320 may be a removable support. As a further example, the kinesiology tape 1300 may be applied to any part of the body of an individual, rather than the leg 1305 as illustrated in FIG. 13.

Figure 14:
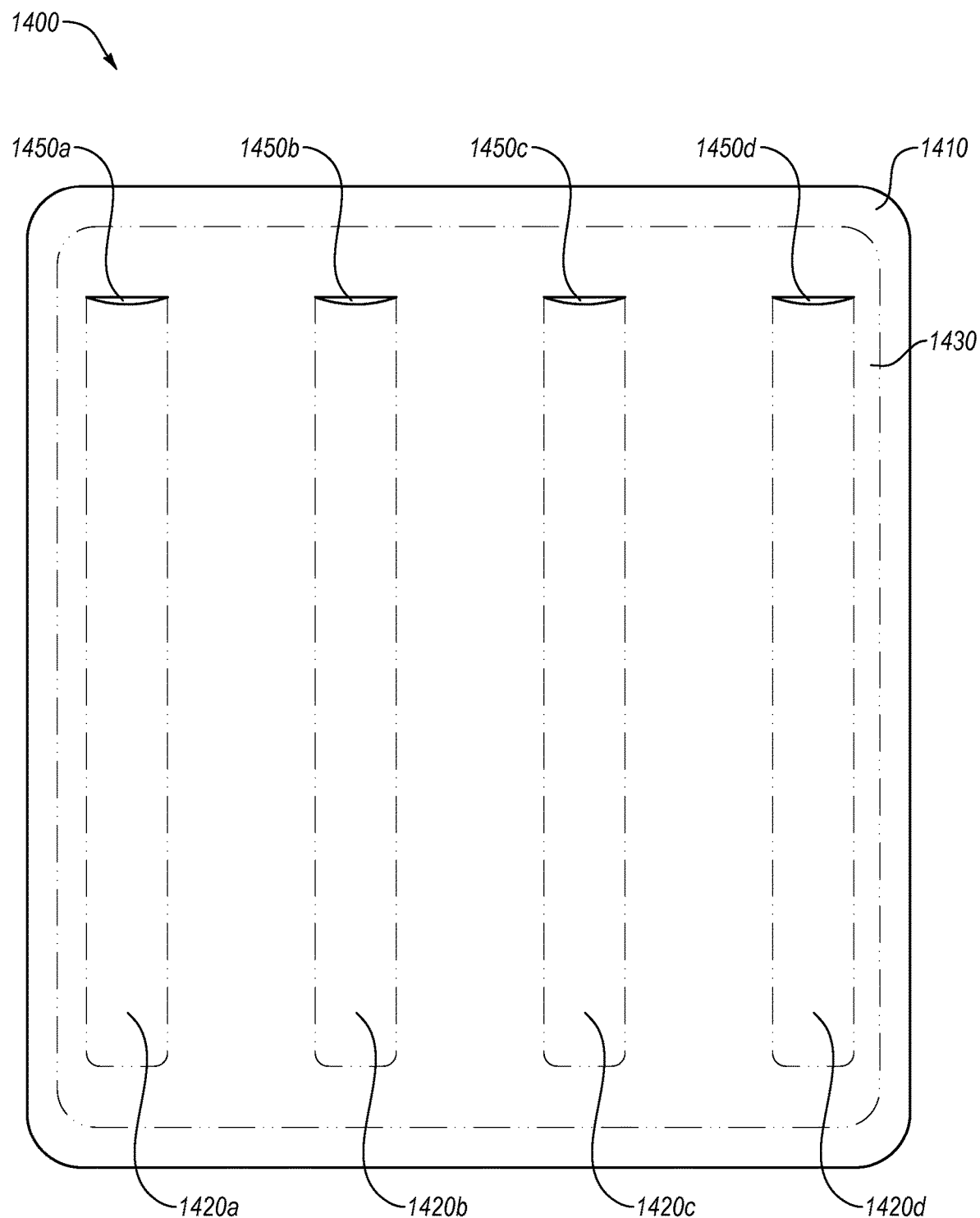
FIG. 14 is a front view of an example of kinesiology tape with receiving portions.

FIG. 14 is a front view of an exemplary of kinesiology tape 1400 with receiving portions 1420. The kinesiology tape 1400 may include a first layer of fabric 1410, a second layer of fabric 1430, receiving portions 1420, such as receiving portions 1420*a*, 1420*b*, 1420*c*, and 1420*d*, and openings 1450, such as openings 1450*a*, 1450*b*, 1450*c*, and 1450*d*.

The first layer of fabric 1410 may be similar to the first layer of fabric 110 of FIG. 1, 810 of FIG. 8, 910 of FIG. 9, 1210 of FIGS. 12, and 1310 of FIG. 13. The second layer of fabric 1430 may be similar to the second layer of fabric 130 of FIG. 1, 830 of FIG. 8, 1230 of FIGS. 12, and 1330 of FIG. 13. The receiving portions 1420 may be similar to the receiving portion 120 of FIG. 1, 820 of FIG. 8, and 920 of FIG. 9. The openings 1450 may be similar to the opening 850 of FIG. 8. The kinesiology tape 1400 may also include an adhesive and/or backing as described with respect to FIG. 1. The kinesiology tape 1400 may be made of similar materials, serve similar purposes, be used in similar ways, etc. as, for example, the kinesiology tape 100 of FIG. 1. FIG. 14 may serve to illustrate the breadth of the present disclosure by showing alternative embodiments of kinesiology tape with multiple supports and/or receiving portions in accordance with the present disclosure.

In some embodiments, the receiving portions 1420 may be aligned in one or more rows along the kinesiology tape 1400. The receiving portions 1420 may not be aligned and may be disposed in any suitable configuration and arrangement depending, for example, upon the intended use of the kinesiology tape 1400. Additionally, the receiving portions 1420 may be in a single line along the kinesiology tape 1400, in multiple lines and/or disposed angles, such as about 30°, 45°, or 60°. It will be appreciated the receiving portions 1420 may also be disposed at other angles, including angles that are larger and/or smaller, and the receiving portions 1420 may be disposed at multiple different angles. In these and other embodiments, by using multiple receiving portions 1420, multiple supports may also be used. Additionally or alternatively, only a single support may be used. For example, an individual may apply the kinesiology tape 1400 and may only removably insert a single support into the kinesiology tape 1400 for a light activity.

In some embodiments, the receiving portions 1420 may be sized and/or configured to receive one or more supports and/or supports of different sizes and configurations. Such a sizing and/or configuration of the receiving portions 1420 may allow, for example, multiple supports to be disposed in a single receiving portion (such as the receiving portion 1420*a*) and that may provide increased support, rigidity, and the like. Such a sizing and/or configuration of the receiving portions 1420 may also allow the kinesiology tape 1400 and/or supports to be customized for particular uses and/or configurations. For example, if a certain degree of support is desired, then one support may be placed in the receiving portion 1420*a*. If additional support is desired, then two or more supports may be placed in the receiving portion 1420*a*. Additional support may also be provided by placing one or more supports in each of the receiving portions 1420*a*, 1420*b*, 1420*c*, and 1420*d*.

In some embodiments, the kinesiology tape 1400 may include one or more of the receiving portions 1420 disposed on the side of the kinesiology tape 1400 with an adhesive and/or on the side of the kinesiology tape 1400 without an adhesive. For example, one or more of the receiving portions 1420 may be on the non-adhesive and/or adhesive side of the kinesiology tape 1400. For example, the receiving portions 1420 may include a slit or opening in the first layer of fabric 1410 with a second layer of fabric 1430 coupled underneath the first layer of fabric 1410. In these and other embodiments, the support may be attached to the adhesive side of the kinesiology tape 1400 or the support may be connected to the adhesive side of the kinesiology tape 1400 by the receiving portions 1420. Additionally or alternatively, the support may also be attached to the adhesive side of the kinesiology tape 1400 by the adhesive. If the support is disposed on the adhesive side of the kinesiology tape 1400, this may allow the support to be connected and/or affixed to skin of an individual. The support may also abut the skin if the support is disposed on the adhesive side of the kinesiology tape 1400. It will be appreciated that the adhesive may cover all or a portion of the support, or the support may be free from the adhesive depending, for example, upon the intended use of the kinesiology tape 1400.

In some embodiments, the kinesiology tape 1400 may be used in a manner similar to a conventional brace or sleeve. Advantageously, because the kinesiology tape 1400 may not provide compressive forces on the affected area and the kinesiology tape 1400 may not surround or encompass the affected area, the kinesiology tape 1400 may allow increased circulation and fluid flow in comparison to a traditional brace or sleeve. Further, because the support may be disposed adjacent or at least proximate the skin, the support may be smaller than a conventional brace or sleeve. Additionally, the kinesiology tape 1400 may be much smaller, more compact and easier to use than a conventional brace or sleeve.

It will be understood that embodiments of the present disclosure may have a variety of shapes, sizes, configurations, and arrangements. It will also be understood embodiments of the present disclosure may include any suitable number and combination of features, components, aspects, and the like. In addition, while embodiments of the present disclosure shown in the accompanying figures may be illustrated as having particular styles, it will be appreciated that the present disclosure may include any suitable style or configuration. Further, one or more embodiments of the present disclosure may be successfully used in connection with other types of objects and devices.

Additionally, to assist in the description of various exemplary embodiments of the present disclosure, words such as top, bottom, front, rear, sides, right, and left are used to describe the accompanying figures which may be, but are not necessarily, drawn to scale. It will further be appreciated that embodiments of the present disclosure may be disposed in a variety of desired positions or orientations, and used in numerous locations, environments, and arrangements.

One of ordinary skill in the art will appreciate after reviewing this disclosure that embodiments of kinesiology tape of the present disclosure may have a variety of shapes, sizes, configurations, and arrangements depending, for example, upon the intended use of the kinesiology tape. One of ordinary skill in the art will also appreciate the various components of the kinesiology tape may have various shapes, sizes, configurations, and arrangements depending, for example, upon the intended use of the kinesiology tape.

Terms used in the present disclosure and especially in the appended claims (e.g., bodies of the appended claims) are generally intended as "open" terms (e.g., the term "including" should be interpreted as "including, but not limited to," the term "having" should be interpreted as "having at least," the term "includes" should be interpreted as "includes, but is not limited to," the term "containing" should be interpreted as "containing, but not limited to," etc.).

Additionally, if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." or "one or more of A, B, and C, etc." is used, in general such a construction is intended to include A alone, B alone, C alone, A and B together, A and C together, B and C together, or A, B, and C together, etc.

Further, any disjunctive word or phrase presenting two or more alternative terms, whether in the description, claims, or drawings, should be understood to contemplate the possibilities of including one of the terms, either of the terms, or both terms. For example, the phrase "A or B" should be understood to include the possibilities of "A" or "B" or "A and B."

All examples and conditional language recited in the present disclosure are intended for pedagogical objects to aid the reader in understanding the disclosure and the concepts contributed by the inventor to furthering the art, and are to be construed as being without limitation to such specifically recited examples and conditions. Although embodiments of the present disclosure have been described in detail, various changes, substitutions, and alterations could be made hereto without departing from the spirit and scope of the present disclosure.

What is claimed is:

1. Kinesiology tape, comprising:
   an application portion comprising:
      a first layer of fabric with an adhesive on a first side of the first layer of fabric; and
      a second layer of fabric coupled to the first layer of fabric, the first layer of fabric and the second layer of fabric forming a receiving portion, the receiving portion shaped to receive a support;
   a backing spanning the first side of the first layer of fabric of the application portion and disposed on the first side of the first layer of fabric; and
   the support within the receiving portion and including:
      a spine extending longitudinally along a length of the application portion; and
      a plurality of teeth extending laterally across the spine and spaced apart from one another, an arrangement of the spine and the plurality of teeth imparting the support with a first bend resistance out of a plane defined by the application portion and a second bend resistance in the plane defined by the application portion, the first bend resistance exceeding the second bend resistance.

2. The kinesiology tape of claim 1, comprising a plurality of application portions formed from a single length of fabric cut between the plurality of application portions.

3. The kinesiology tape of claim 2, wherein the backing is formed from a single length of material.

4. The kinesiology tape of claim 3, wherein the backing is partially cut between the plurality of application portions.

5. The kinesiology tape of claim 2, wherein the cut between the plurality of application portions is a partial cut.

6. The kinesiology tape of claim 2, wherein the cut between the plurality of application portions is a complete cut such that each of the plurality of application portions is disconnected from other application portions.

* * * * *